(12) United States Patent
Dam

(10) Patent No.: US 7,661,294 B2
(45) Date of Patent: Feb. 16, 2010

(54) NON-INVASIVE MULTI-FUNCTION SENSOR SYSTEM

(75) Inventor: Naim Dam, Muttontown, NY (US)

(73) Assignees: Cosense, Inc., Hauppauge, NY (US); Fresenius Medical Care Holdings, Inc., Waltham, MA (US)

( * ) Notice: Subject to any disclaimer, the term of this patent is extended or adjusted under 35 U.S.C. 154(b) by 229 days.

(21) Appl. No.: 11/903,261

(22) Filed: Sep. 21, 2007

(65) Prior Publication Data

US 2009/0078047 A1    Mar. 26, 2009

(51) Int. Cl.
*G01N 29/024* (2006.01)
*A61M 37/00* (2006.01)
*G01N 29/032* (2006.01)
*G01J 5/28* (2006.01)

(52) U.S. Cl. .................. 73/19.03; 73/61.75; 73/597; 73/598; 250/343; 604/6.08

(58) Field of Classification Search ............... 73/579, 73/597, 598, 19.03, 61.75; 250/343; 604/6.08
See application file for complete search history.

(56) References Cited

U.S. PATENT DOCUMENTS

| | | | |
|---|---|---|---|
| 3,921,622 A * | 11/1975 | Cole ..................... | 600/437 |
| 4,797,655 A * | 1/1989 | Orndal et al. ............ | 340/521 |
| 4,909,786 A * | 3/1990 | Gijselhart et al. ......... | 604/65 |
| 5,179,862 A * | 1/1993 | Lynnworth .............. | 73/861.28 |
| 5,392,638 A * | 2/1995 | Kawahara ............... | 73/61.49 |
| 5,394,732 A * | 3/1995 | Johnson et al. .......... | 73/19.1 |
| 6,622,542 B2 * | 9/2003 | Derek et al. ............ | 73/19.03 |
| 7,243,541 B1 | 7/2007 | Bey et al. | |
| 7,481,114 B2 * | 1/2009 | Lynnworth .............. | 73/597 |
| 2006/0277977 A1 | 12/2006 | Kahn et al. | |
| 2008/0098798 A1 * | 5/2008 | Riley et al. ............. | 73/19.03 |

FOREIGN PATENT DOCUMENTS

| KR | 10-0157986 B1 | 11/1998 |
|---|---|---|
| KR | 10-2002-0063001 A | 7/2002 |
| KR | 10-0516727 B1 | 9/2005 |

* cited by examiner

*Primary Examiner*—Hezron Williams
*Assistant Examiner*—Rose M Miller
(74) *Attorney, Agent, or Firm*—Gordon D. Coplein

(57) ABSTRACT

An integrated multi-function sensor system has a head having a slot to accept a tube of a deformable material and a plurality of sensor elements mounted in the walls of the head slot to confront a tube in the slot, each sensor element being for affecting sensing of a condition relating to a liquid in the tube. An integrated electronic circuit including a microprocessor operates to determine the various conditions of a liquid flowing in the tube sensed by the sensor elements, which conditions include detection of air bubbles and/or particles by ultrasonic sensing elements, detection of an occlusion in the liquid flow by sensing the deformation of the tube wall by a force sensing element, determining the temperature of the liquid by an infrared temperature sensing element, and determining the color of the liquid by optical elements.

16 Claims, 5 Drawing Sheets

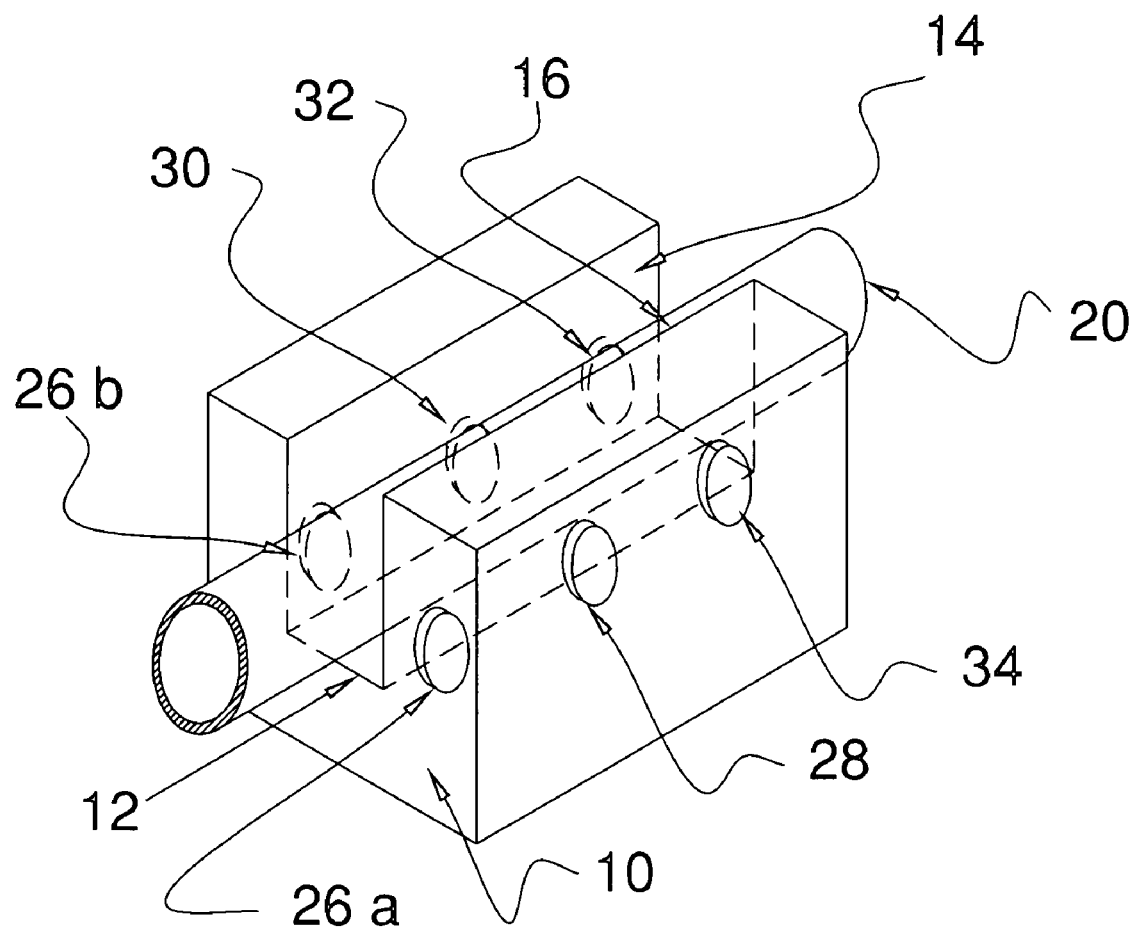
FIG: 1

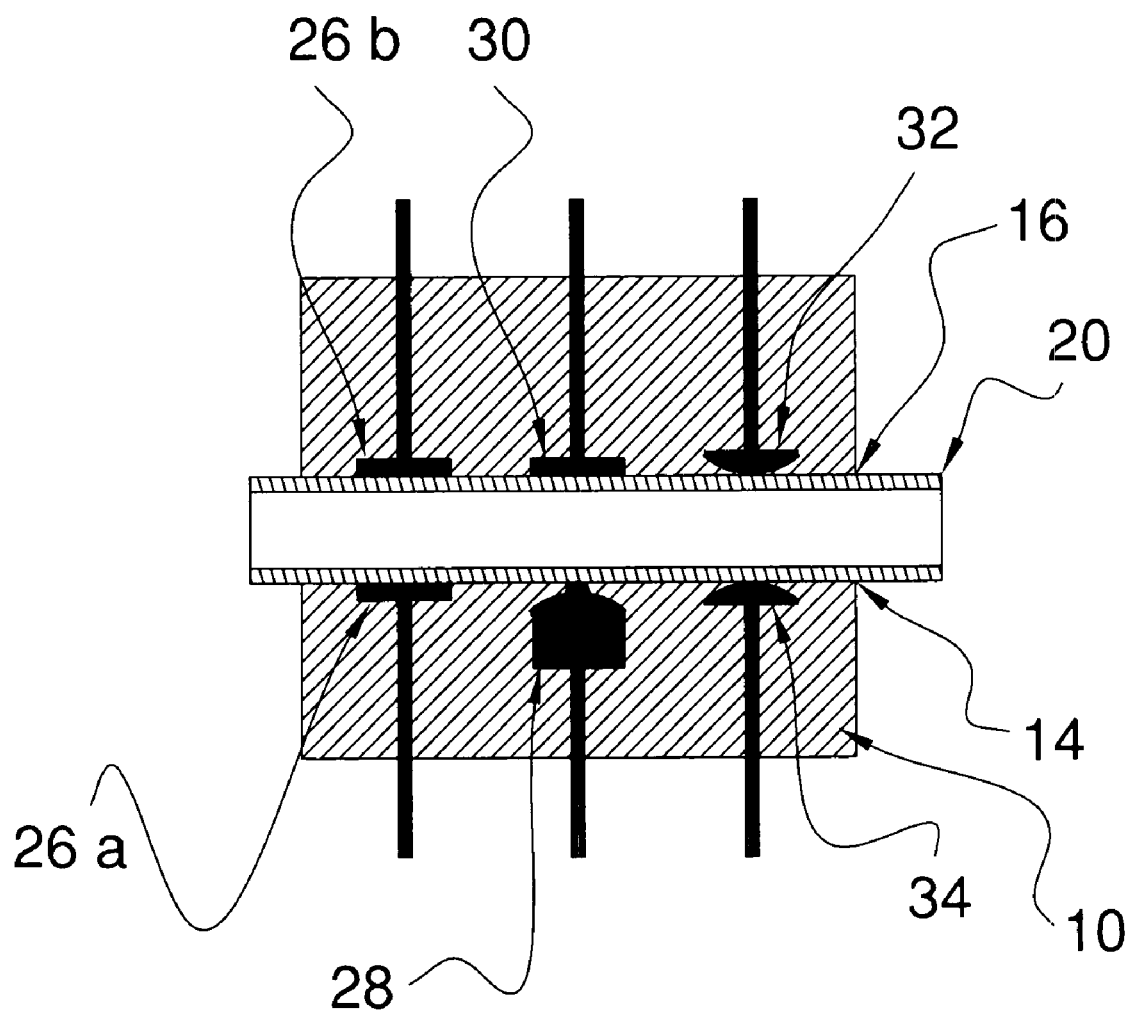
FIG: 2

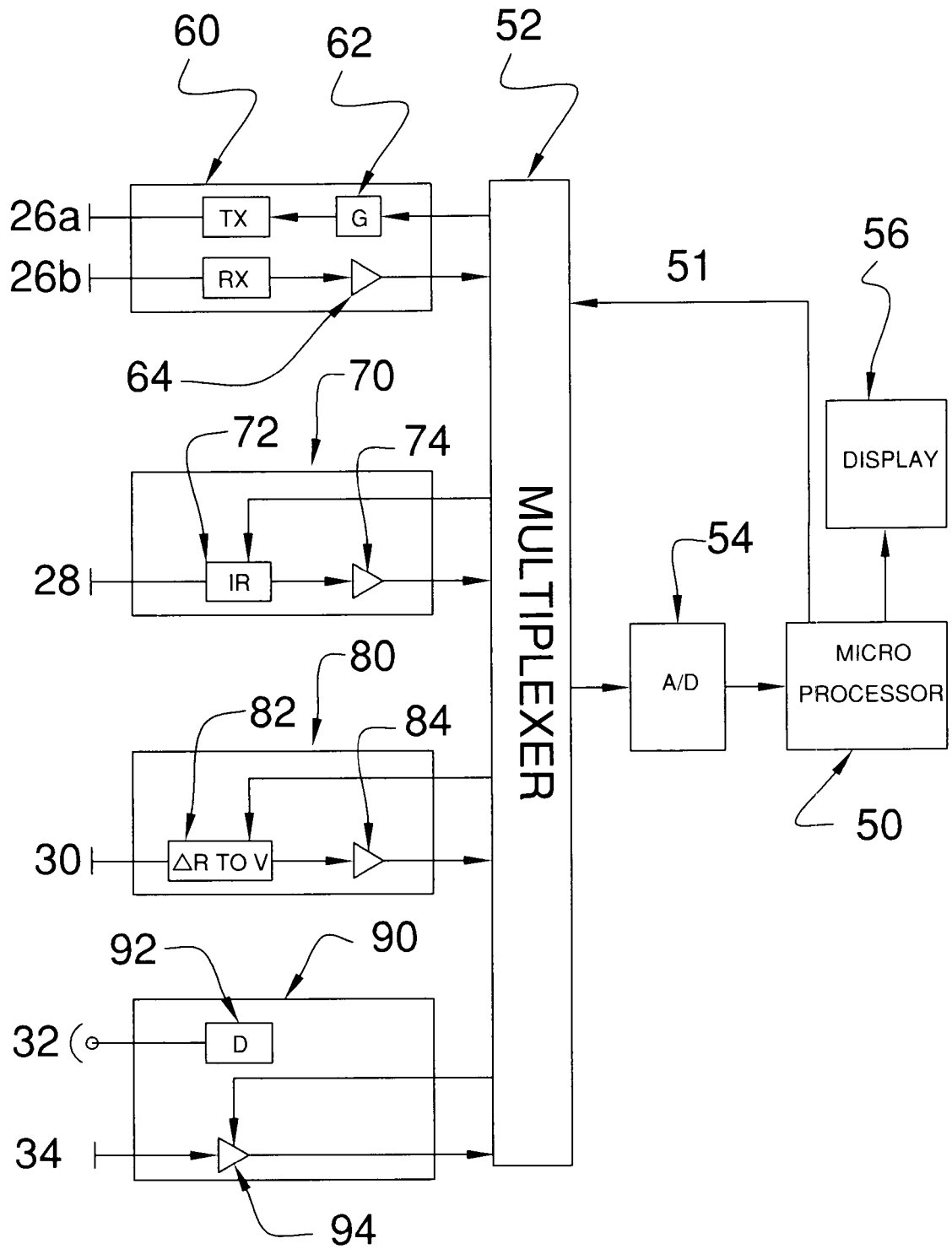
FIG: 3

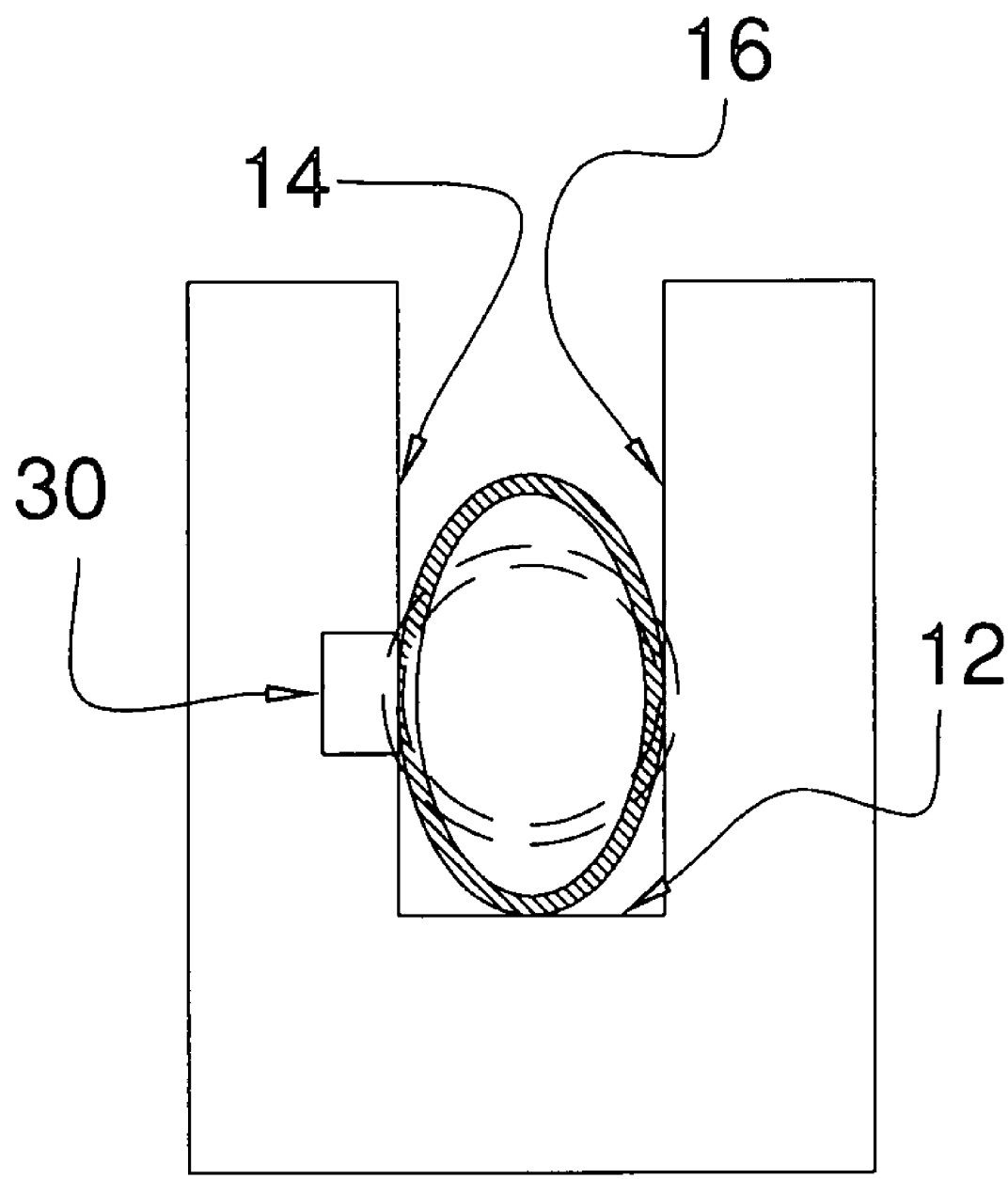
FIG: 4

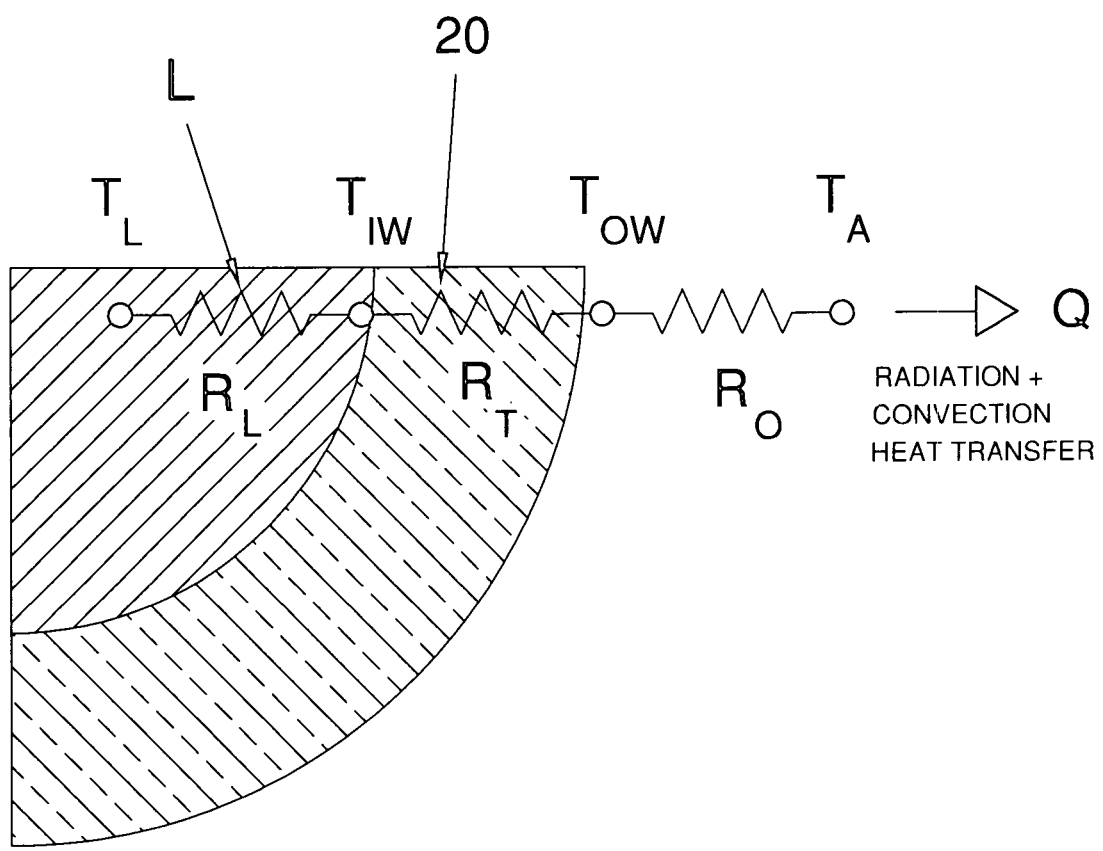
FIG: 5

NON-INVASIVE MULTI-FUNCTION SENSOR SYSTEM

FIELD OF THE INVENTION

The present invention is directed to a sensor system utilizing a multi-function sensor head having sensor elements that can perform non-invasively multiple functions such as sensing the temperature of a liquid flowing in a tube, sensing and characterizing air bubbles and/or particles present in the liquid as well as sensing the type of the liquid and sensing an occlusion in the liquid flow.

BACKGROUND OF THE INVENTION

In certain applications in medical equipment such as kidney dialysis machines, infusion pump blood analyzers, transfusion systems, cardio-pulmonary bypass machines and the like, an attempt is made to ensure patient safety. In these applications flexible plastic tubes are used to for tasks such as to supply the patient with medication, supply saline solution, extract fluid such as blood from the patient's body and supply it back after cleansing or purification, as well as for other functions. For example, during a kidney dialysis process tubes are connected to both the vein and artery of the patient for the blood extraction and return after cleansing. Another tube is used for infusion of medicine.

For each tube connected to the patient's body it is desirable and even necessary to monitor different conditions relative to the liquid flowing in the tube and even conditions concerning the tube itself. For example, it might be required or desirable to sense the temperature of the liquid flowing in the tube, sense the presence of air bubbles and/or particles present in the liquid and to characterize these as to size and quantity. Sensing of other conditions include that of the type of liquid, such as blood or a clear saline solution, flowing in the tube as well as sensing an occlusion in the flow. It is even desirable to sense that a required tube is connected to the patient.

In the prior art, a separate sensor and an associated electronic circuit is used to perform each of the sensing functions. This complicates the use of the medical equipment in that each of the sensors has to be mounted to the one or more tubes. For example, several different sensors are separately mounted to a single tube to sense conditions that are supposed to be monitored relative to the liquid flowing in that tube. This requires a selection process by the medical technician. It also makes use of the medical equipment more cumbersome in terms of operation, size and also makes it more costly. Also, since a different sensor and its associated electronic circuit is required to monitor each of the different conditions, the reliability of the entire system of the medical equipment and sensors decreases because the failure mode possibility increases due to the use of multiple and separate sensors each having a dedicated electronic circuit. Further, the user of the equipment often needs to coordinate with multiple vendors to purchase different sensors and different electronic circuits for different functionality. Accordingly, a need exists for apparatus that can overcomes these many problems and disadvantages.

BRIEF DESCRIPTION OF THE INVENTION

The present invention is directed to a system that can perform a plurality of sensing functions and that includes an integrated multifunction sensing module to eliminate the above problems. In the invention, the module has a head that has a slot into which the tube is to be placed. The head incorporates a plurality of sensor elements such as those needed for air bubble detection, temperature sensing and pressure sensing for use in sensing occlusions in the fluid flow in the tube and to also to give an indication of the tube being positively connected to the head. The head also includes a light emitting device, such as an LED, that transmits a light beam into the tube in the slot and a photodetector that receives the light. This permits a determination of weather the fluid in the tube is blood or a more clear liquid, such as saline solution or a flow of medicament. The module head is formed of a block of material, such as a clear polycarbonate plastic, that has a slot with opposing side walls on which the various sensor elements are mounted. The tube is laid in the slot and is contacted by those of the sensing elements that need physical contact to perform its function. The leads from the various sensor elements mounted in the head are connected to an electronic circuit that includes a microprocessor that is programmed to perform the various functions related to the sensor elements mounted in the head. The electronic circuit preferably includes a multiplexer so that a single microprocessor can be used to control all sensing functions.

BRIEF DESCRIPTION OF THE DRAWINGS

Other objects and advantages of the present invention will become more apparent upon reference to the following specification and annexed drawings in which:

FIG. 1 is a perspective view of the integral multi-function sensor head;

FIG. 2 is a cross section of the head of FIG. 1;

FIG. 3 is a block diagram of the electronic circuit of the system;

FIG. 4 is a cross-sectional view showing tube deformation; and

FIG. 5 is a view that explains operation of the infrared sensor used to measure temperature of a liquid in the tube.

DETAILED DESCRIPTION OF THE INVENTION

Referring to FIGS. 1 and 2, the integral multi-function sensor of the invention has a head 10 that is a block of a plastic material such as UDEL polysulfone resin manufactured by Solvay Advanced Polymers. The head 10 is illustratively shown as being a generally rectangular shape and can be molded by any suitable technique. In the head 10 there is a longitudinal slot 12 that has opposing side walls 14 and 16. A tube 20 of flexible and elastically outwardly expansible plastic material having a liquid flowing in it is to be placed in the slot 12. The tube 20 is to have one end connected to the body of a patient and the other end connected to a liquid supply, such as a medicine or saline solution, or to a machine such as a dialysis machine. In the molding of the head 10 a number of depressions are formed in the opposing slot side walls 14 and 16. Different types of sensor elements, to be described below, are mounted in the depressions and each depression is of a shape to accommodate the particular type of sensor element that is to be mounted in it. The slot side wall thickness is typically 0.30" to 0.050" depending upon plastic material and the sensor elements used. A hole is drilled through the outside wall of the head 10 to each of the depressions in the slot sidewall 14 and 16 to accommodate a respective lead wire or wires connected to the respective sensor element.

Considering the sensor elements, near one end of the head 10 is a pair of piezoelectric elements 26a and 26b mounted opposing each other in the slot opposing slot side walls 14 and 16. Near the center of the head 10 a temperature sensor 20 is mounted in one of the slot side walls 14 and a force sensor 30 is mounted in the other sidewall 16. Near the other end of the head 10 a light emitting element 32, such as an LED, is mounted in the side wall 14 and a photodetector 34 is mounted opposing it in the side wall 16. The representation of the shapes of the various sensor elements are in schematic form and the shape will depend upon the specific sensor element that is used. The placement of the various sensor elements also can be varied. Each of the sensor elements is held in its respective depressions by a suitable adhesive, such as an epoxy, and the lead wires for each sensor element pass out through the walls of the head that form the slot to be exterior of the head so as to be able to be connected to an electronic circuit, to be described below.

In the operation of the system of the invention, the plastic tube 12 is laid in the slot 12 of the head 10. The width of the slot 12 is slightly less than the outer diameter of the plastic tube 20 so that the faces of the sensor elements 26, 28 and 30 mounted in the opposing slot side walls 14 and 16 that need to be in contact with the tube 20 makes such contact. A typical deformation or squeeze of the tube in the slot would be 15% to 20% of the tube outer diameter. The light emitting element 32 and photo transistor 34 optical elements need not necessarily make contact with the wall of the plastic tube but one or both of these elements can make such contact. A description of individual sensor elements and their respective functions follows.

The piezoelectric elements 26a and 26b are of any suitable material used in ultrasonic technology, such as PZT or PVDF material. In the integral multi-function sensor system of the invention, the piezoelectric elements 26a and 26b operate as part of an air bubble detection and characterization apparatus. In such an apparatus, ultrasonic energy is supplied to one of the piezoelectric elements 26 and is transmitted though the tube 20 to be received by the other element. A circuit of this type is described in U.S. patent application Ser. No. 11/703,025, filed Feb. 7, 2007 for "Ultrasonic System for Detecting and Quantifying of Air Bubbles/particles in a Flowing Liquid", which is assigned to the assignee of this application and whose disclosure is incorporated herein by reference. This system is briefly described below with reference to FIG. 3. Other ultrasonic type systems also can be used to detect air bubbles.

The temperature sensor element 28 preferably is an infrared thermocouple, an example being P/N: 150042, Model No C UIRT-K-98.6f/37C manufactured by Exergen, Watertown, Mass. This device has the ability to measure the internal temperature of the liquid in the tube 20 non-invasively by measuring both tube surface temperature and the ambient temperature. It is preferred that the sensor element 28 is mounted in the head 10 so as to converge the sensor infrared beam at a focus point in the middle of tube 20 to measure fluid temperature accurately.

The operation of the temperature sensor element 28 is described referring to FIG. 5. As seen in FIG. 5, a liquid L flowing in a tube such as the tube 20 having a temperature $T_L$ which is represented by thermal resistance $R_L$ transfers heat by conduction to the tube inside surface $T_{IW}$, which in turn conducts heat to the tube external surface $T_{OW}$. This transfer is represented by the thermal resistance $R_T$. The heat on the tube outer wall is transferred to the environment via radiation and convection as represented by thermal resistance Ro. Using the method of thermal analysis with electrical analogs: current=heat flow and voltage=temperature, the heat transfer equation may be written as follows:

$$Q = \frac{1}{R_L + R_T + R_O}(T_L - T_A)$$

where

Q=Heat transfer, and $R_L + R_T = R_O$

For heat balance:

$$Q = \frac{1}{R_O}(T_{OW} - T_A)$$

Accordingly, $$T_L = \frac{R_L + R_T + R_O}{R_o}(T_{OW} - T_A) + T_A$$

The infrared sensor 28 measures both $T_{OW}$ and $T_A$. The output lead of sensor 28 is connected to a suitable circuit that includes an analog to digital converter and other necessary circuit for converting the change in temperature measured by the sensor 28 into a digital value and a suitably programmed microprocessor or similar device to automatically solve the equation for the liquid temperature $T_L$. The technique used has been found to be able to measure the liquid temperature with an accuracy of ±0.2° C. The measurement is done non-invasively and provides a highly accurate method of monitoring the temperature of interest. The measured value of the liquid temperature can be used for control purposes, such as turning on and off heating and cooling units or to advise the system operator of changes in temperature.

Sensor element 30 is a force/pressure sensor that accomplishes non-invasive measurement of the internal pressure of the elastic tube 20. During dialysis or infusion of a medicine, the internal pressure of the liquid in the tube 20 exerts force on the inner wall of the tube which is transmitted to the tube outside wall. The force exerted on the tube outer wall has a linear relationship with the tube internal pressure. As shown in FIG. 4, a tube 20 placed in the slot 12 with no liquid flowing in it has a somewhat elliptical shape. Liquid flowing through the tube causes it to expand to a more circular shape a shown by the dash lines. The outer tube wall expansion is measured using a force or strain gauge pressure sensor 30 which is commercially available. A suitable force sensor element is P/N: DEL 2239 equivalent and manufactured by Strain Measurement Device, Meriden Conn. The face of the sensor element 30 contacts the outer wall of the tube laid in the slot 12. Such force or strain gauge devices produce a change in resistance as a measurement of the force sensed.

The force sensor 30 is used to perform several functions. It detects an occlusion in the tube by sensing a sudden change in pressure of the liquid in the tube 20. There also will be drop in pressure in the case of a pump failure occurs. The sensor 30 also detects the presence of a tube in sensing slot 12. That is, insertion of the tube 20 in the slot 12 exerts a force against the sensor element 30. The sensor 30 differentiates between dry and liquid presence conditions in the tube. That is, when liquid flows in the tube 20 the force on the tube outer wall will be greater than if there is no liquid flowing in the tube.

The sensor elements 32 and 34 provide for detection of the type of liquid flowing in the tube 20. A typical use would be in detecting if there is blood, or a similar dark liquid, or a clear liquid, or a saline solution, which is relatively clear. Another use is to detect if there is any liquid in the tube or if it is dry. The light emitting element 32 is a suitable device, such as an Infrared emitting diode, and the light receiving element 34 a suitable device, such as a silicon photo transistor. The light emitting element 32, which can be an infrared energy emitting diode, is positioned so as to have its output beam focused in the center of the tube 20. A constant current source is used to drive infrared emitting diode. The photo transistor 34 receives the light energy transmitted through the tube 20. The optical transmission through the tube and a liquid flowing through it is amplified and an amplified analog signal is digitized and analyzed by a microprocessor, as described below.

The optical elements 32 and 34 accomplish a number of functions. There is a detection of blood vs saline solution since the amount of light passing through the liquid will be of different amplitudes. Different amplitudes of light will be detected by the detector 34 when there is no tube in the slot, tube with a clear liquid flowing in it, and a tube with blood inside the tube. All of these different conditions can be recognized and different indications given to the operator of the equipment.

In certain applications it is important to detect presence of a tube in the slot before fluid is injected. Buy combining the pressure and optical sensing techniques described above, the system of the invention provides added reliability to sense tube presence or absent conditions.

FIG. 3 is a block diagram of an electronic circuit that can be used with the multi-function sensor of the invention. The circuit of FIG. 3 is integral in that one microprocessor is used to control all of the measuring functions for all of the sensors mounted in the head. While this is preferred, other circuits can be used, for example, a separate circuit with its own microprocessor and display for each different type of sensor. Also, it is not necessary to utilize all of the sensor elements of the head 10. For example, in a particular use it might not be necessary to measure one of the conditions measured by one of the sensor elements.

Referring to FIG. 3, there is a microprocessor 50 that is suitably programmed to perform all of the functions described below. That is, the microprocessor 50 outputs the necessary signals to control the operation of each of the several sensor elements to perform its intended function and to produce an output measurement. The microprocessor 50 also has an output on line 51 that controls operation of a bi-directional multiplexer 52 that is gated by the microprocessor to sequentially apply the signals from the microprocessor 50 to control operation of an air bubble detection and characterization circuit 60 associated with the piezoelectric sensor elements 26a and 26b, a temperature sensing circuit 70 associated with sensor element 28, a pressure sensing circuit 80 associated with the force sensor 30, and a liquid detection circuit 90 associated with the optical elements 32 and 34. An analog to digital converter 54 digitizes an analog output signal from any of the circuits 60, 70, 80 and 90 and applies it to the microprocessor 50 for processing for producing the proper output depending upon the sensor element that is active. The microprocessor 50 drives a visual display device 56 to display measurement results, warnings, and other information. The microprocessor also can produce outputs to other devices such as printers, audio alarms, RS 232 output, etc. All of this is conventional in the art.

The air bubble and particle sensing circuit 60 is gated on for operation by the multiplexer 52 for a predetermined time by the microprocessor 50. Considering the air bubble detection and characterization circuit 60, as described in the aforesaid patent application Ser. No. 11/703,025, energy in the ultrasonic frequency range, for example 2-5 MHz, is supplied by a generator 62 to the element 26a or 26b that is to be the transmitter element to be transmitted to the opposing other element which serves as a receiver element. The received ultrasonic energy is amplified in an amplifier 64 and detected and preferably split by a suitable circuit into a steady state (DC) component and a varying or transient (AC) component, the components respectively being indicative of the absence and the presence of an air bubble or a particle in the liquid. The two components of the signal are applied to the A/D converter 56 whose output is supplied to microprocessor 50 which uses the digital data that corresponds to the presence of a varying transient component to indicate the presence of an air bubble and/or a particle and to determine its characteristics. When liquid is flowing through the tube 20 the presence of the steady-state component indicates that the system is operating properly to provide a continuous self check against system malfunction.

The temperature sensing circuit 70 is any suitable conventional circuit used to measure temperature based on infrared (IR) energy. Such circuits are well known in the art. When gated on by the microprocessor 50 through the multiplexer 52, the temperature sensing circuit 70 electronics 72 produces the IR beam of energy that heats the wall of the tube 20 in the manner described with respect to FIG. 5. and produces an analog output voltage that is amplified by an amplifier 74. The analog output is applied to the analog to digital converter 54 and the digital output applied to the microprocessor for processing and display.

The force sensing circuit 80 that uses the sensor element 30 has a circuit, such as a bridge circuit, that converts the change of resistance of the sensor element in response to the force or pressure into a voltage that is applied to an amplifier 84 and then through the multiplexer 52 to the analog to digital converter 54. The measured force represented by the analog voltage is converted into digital format to be used by the microprocessor 50 and to be displayed on the display 56.

The liquid color sensing circuit 90 has a drive circuit 92 for the light emitting element 92 which preferably is left on at all times when the system is operating. An amplifier 94 that is gated on by signals from the microprocessor 50 permits the signal generated from the light passing through the tube 20 and/or liquid that is received by the photo transistor 34 to pass through the multiplexer 52 to the analog to digital converter 54. As explained above, the amplitude of the signal produced by the photo transistor corresponds to the absence of liquid in the tube and the color of the liquid. After processing of the digital signal by the microprocessor the results are displayed on the display 56.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. An integrated multi-function sensor system comprising:
   a head having a slot to accept a tube of a deformable material;

a plurality of sensor elements mounted in said head to confront a tube in said slot, each said sensor element for affecting sensing of a condition relating to a liquid in the tube; wherein said plurality of sensor elements comprise:
a pair of piezoelectric elements mounted opposing each other on the side walls of said slot, one of said piezoelectric elements of said pair to transmit ultrasonic energy through the outer wall of a tube in the slot to be received by the other of said piezoelectric elements of said pair; and
a force sensor mounted on one wall of said slot to contact the outer wall of a tube in said slot; wherein each of said plurality of sensor elements performs its respective sensing function while being located outside of the wall of a tube in said slot; and
an electronic circuit to which said plurality of sensor elements are connected to provide a measurement of the condition sensed by each of said plurality of sensor elements, wherein said electronic circuit comprises:
a microprocessor;
an air bubble and particle detection circuit controlled by said microprocessor to cause ultrasonic energy to be transmitted by said one piezoelectric element though the tube to be received by said other piezoelectric element, and to determine from the received energy the presence of air bubbles and/or particles in liquid flowing in a tube in the slot; and
a force detection circuit controlled by said microprocessor to determine from a change in deformation of a tube in said slot a change in pressure of a liquid flowing in the tube which indicates an occlusion of the liquid flow.

2. An integrated multi-function sensor system as claimed in claim 1 wherein said force detection circuit also acts to determine the presence or absence of a tube in said slot.

3. An integrated multi-function sensor system as claimed in claim 1 wherein said plurality of sensor elements further comprise:
an infrared temperature sensor element that projects a beam of infrared energy into a tube in said slot; and
a light emitting element mounted on one wall of the slot to transmit light into the interior of a tube in the slot and a light receiving element on the opposing wall of said slot to receive the light passing trough the tube; and wherein said electronic circuit further comprises:
a temperature sensing circuit responsive to the infrared energy sensed by said infrared temperature sensing element to determine the temperature of the liquid flowing in a tube in said slot; and
a liquid type detection circuit responsive to the light received by said light receiving element to determine the color of the liquid flowing in a tube in said slot.

4. An integrated multi-function sensor system as claimed in claim 3 wherein said liquid type detection circuit also operates to determine the absence of a tube in said slot and/or the presence of liquid flowing in the tube.

5. An integrated multi-function sensor system as claimed in claim 3 wherein said electronic circuit further comprises a multiplexer controlled by timing signals to separately actuate each of said air bubble and/or particle detection circuit, said force sensing circuit, said temperature sensing circuit and said liquid type detection circuit.

6. An integrated multi-function sensor system as claimed in claim 1 wherein said electronic circuit further comprises a multiplexer controlled by timing signals to separately actuate each of said air bubble and/or particle detection circuit and said force sensing circuit.

7. A sensor head for an integrated multi-function sensor system comprising:
a head having a slot to accept a tube of a deformable material; and
a plurality of sensor elements mounted in said head to confront a tube in said slot, each said sensor element for affecting sensing of a condition relating to a liquid in the tube wherein said plurality of sensor elements comprise:
a pair of piezoelectric elements mounted opposing each other on the side walls of said slot to oppose the outer wall of a tube in the slot; and
a force sensor mounted on one wall of said slot to contact the outer wall of a tube in said slot.

8. A sensor head for an integrated multi-function sensor system comprising:
a head having a slot to accept a tube of a deformable material; and
a plurality of sensor elements mounted in said head to confront a tube in said slot, each said sensor element for affecting sensing of a condition relating to a liquid in the tube wherein said plurality of sensor elements comprise:
an infrared temperature sensor element that projects a beam of infrared energy into a tube in said slot; and
a light emitting element mounted on one wall of the slot to transmit light into the interior of a tube in the slot and a light receiving element on the opposing wall of said slot to receive the light passing trough the tube.

9. A sensor head as claimed in claim 8 wherein said plurality of sensor elements further comprises:
a pair of piezoelectric elements mounted opposing each other on the side walls of said slot, one of said elements of said pair to transmit ultrasonic energy through the outer wall of a tube in said slot to be received by the other of said elements of said pair.

10. An integrated multi-function sensor system as claimed in claim 9 wherein each of said plurality of sensor elements performs its respective sensing function while being located outside of the wall of a tube in said slot.

11. A sensor head as claimed in claim 9 wherein said head is made of a transparent plastic material.

12. A sensor head as claimed in claim 9 and further comprising:
an electronic circuit to which said plurality of sensor elements are connected to provide a measurement of the condition sensed by each of said plurality of sensor elements.

13. A sensor head as claimed in claim 12 where said electronic circuit comprises:
a microprocessor;
an air bubble and particle detection circuit controlled by said microprocessor to supply electrical signals to said one piezoelectric element of said pair to be transmitted through a tube in said slot to be received by the other said element of said pair, and to determine from the received energy the presence of air bubbles and/or particles in liquid flowing in the tube;
a temperature sensing circuit responsive to the infrared energy sensed by said infrared temperature sensing element to determine the temperature of the liquid flowing in the tube; and
a liquid type detection circuit responsive to the light received by said light receiving element to determine the color of the liquid flowing in the tube.

14. An integrated multi-function sensor system as claimed in claim 13 wherein said liquid type detection circuit also operates to determine the absence of a tube in said slot and/or the presence of liquid flowing in the tube.

15. An integrated multi-function sensor system as claimed in claim 13 wherein said electronic circuit further comprises a multiplexer controlled by timing signals to separately actuate each of said air bubble and/or particle detection circuit, said temperature detecting circuit, and said liquid type detecting circuit.

16. A sensor head as claimed in claim 8 and further comprising:
 a force sensor mounted on one wall of said slot to contact the outer wall of a tube in said slot.

* * * * *